United States Patent [19]

Reese

[11] Patent Number: 5,157,332

[45] Date of Patent: Oct. 20, 1992

[54] THREE-TOROID ELECTRODELESS CONDUCTIVITY CELL

[75] Inventor: Philip C. Reese, Buzzards Bay, Mass.

[73] Assignee: The Foxboro Company, Foxboro, Mass.

[21] Appl. No.: 421,484

[22] Filed: Oct. 13, 1989

[51] Int. Cl.$^5$ .................. G01N 27/02; G01N 27/74
[52] U.S. Cl. .................. 324/445; 324/441; 324/439; 324/204
[58] Field of Search ............ 324/204, 439, 442, 445, 324/446, 441, 448–450, 342; 73/861.08, 861.11

[56] References Cited

U.S. PATENT DOCUMENTS

| | | | |
|---|---|---|---|
| 2,435,043 | 1/1948 | Lehde et al. | 324/204 X |
| 2,987,668 | 6/1961 | Gondouin | 324/342 |
| 3,396,331 | 8/1968 | Sperry, III | 324/445 |
| 4,220,920 | 9/1980 | Gross | 324/445 X |
| 4,816,758 | 3/1989 | Theissen et al. | 324/204 |

OTHER PUBLICATIONS

Industrial Instruments Inc, Electrolyte Conductivity Equipment, copyright Dec. 1963, catalog 27.

Primary Examiner—Jack B. Harvey
Attorney, Agent, or Firm—Wigman & Cohen

[57] ABSTRACT

An electrodeless conductivity measuring cell having three toroids. In one arrangement, the three toroids are stacked together wherein the center toroid is used for sensing and the two outer toroids are the drive toroids. Alternatively, the center toroid may be used as the drive coil and the outer toroids used as sense coils. Washer-shaped, grounded discs are placed between the outer toroids and the center toroid to provide for improved noise rejection. A method of validating the fluid conductivity measurement of such a measuring cell. The fluid conductivity is measured with a three-cell configuration, and then it is measured with a two-cell configuration. If the conductivity is observed to be the same, the cells are likely functioning normally. If fluid leaks into the cell cavity, the measurement of conductivity will change.

37 Claims, 3 Drawing Sheets

THREE-TOROID ELECTRODELESS CONDUCTIVITY CELL

TECHNICAL FIELD

This invention is to be used to measure the electrical conductivity of fluids. In this class of instruments, a first driven toroidal magnetic circuit induces a magnetic field in a fluid surrounding the driven toroid core, and a second toroidal magnetic circuit is used to sense the magnetic field in the liquid. As used herein, "toroid" will refer to the ordinary toroidal coil electromagnet, and preferably includes an electromagnetic coil or a coil winding of toroidal shape. The electrical conductivity of the fluid is then sensed by measuring the second sensing coil electrical output.

This invention is used for measurement of the conductivity of fluids such as are found in pipes used in chemical processing. For example, measurement of a fluid having a percentage of an acid will produce a known conductivity value of the fluid mixture. It is, therefore, possible to regulate the percentage of acid flowing in a pipe by measuring and adjusting the acid flow to achieve the desired conductivity. Ionic impurities in discharge fluids may also be measured.

BACKGROUND ART

It is well known to construct measuring probes for fluid conductivity measurement by placing a first magnetic field generating toroid coil in an arrangement relative to a second, magnetic field measuring toroid coil where the conductivity of a fluid magnetically couples the coils. Typical devices known in the art also include placement of a signal source coil and a receiving coil on separate fluid paths as in U.S. Pat. No. 2,709,785 to Fielden.

The principal of fluid measurement by magnetic measurements is discussed in U.S. Pat. Nos. 2,642,057, 3,806,798 and 4,220,920.

An Industrial Instruments Inc. Catalog 27, believed copyrighted in 1963, discusses solution conductivity measurement and theory. This catalog is believed to have been classified by the United States Patent Office in class 324 subclass 439.

The conventional configuration of the toroid coils in the prior art has been the placement of a first toroid coil apart from a second one, where one carries a current and the other is used for measurement.

The conductivity of the solution surrounding the cell and within the cylindrical bore provides link-coupling between the toroid windings for the transfer of electromagnetic energy between the two toroid windings. There is a direct ratio between the conductivity of the fluid being measured and the amount of energy transferred to the receiving toroid coil with a given cell factor (constant). The cell factor is governed by the ratio of the length of the cell to the cross-sectional area of the bore. Therefore, a doubling of the length will double the cell factor.

This type of cell has been used extensively in the measurement of fluids in the order of 10 (100 microsiemens/cm) to 2000 (500 microsiemens/cm) ohms. In order to make measurements below 500 microsiemens/cm the cell must be made with a very low cell factor, and a high-gain electronic circuit must be used to detect the signal. Under these circumstances a large noise factor is often present in the measurement. This noise comes from the solution being measured and from the high-gain electronic circuit which must be used. The presence of this noise makes it very difficult to make accurate and reliable measurements.

DISCLOSURE OF INVENTION

This invention uses three toroidal coils assembled side by side to form a cylindrical bore hole which is coaxial with the toroid center lines. The outer two toroids may be either drive coils or receiving coils. It has been found that the highest signal-to-noise ratio is achieved where the outer toroids are the driven coils. When the receiving toroid is located in the center of the stack of three toroids, it is shielded from noise generated in the solution to be measured.

In this invention, the dual driven toroids allow the signal being received at the electronics to be twice as large as a signal from a two-toroid cel prior art with the same cell factor. The improved electrical cell factor and the dual drive coil configuration of this invention minimize the noise present in the measurement and also permits more sensitive measurements when the receiving coil current approaches zero.

The input signal to the drive coils is preferably an ac voltage and the measurement by the receiving coil is measurement of the alternating current flowing through it.

An important feature of this configuration is the provision of convenient testing of a measurement cell where there has been fluid leakage into any one of the toroids of the cell cavity. One of the two drive toroids may be switched into and out of the circuit during a measurement. The fluid is first measured with all three coils present and then it is measured with one drive drive coil and one sense coil. The conductivity measurement must remain the same in either state (for a given fluid electrical conductivity) or it will indicate that the measurements are unreliable and possibly some of the solution has penetrated into the toroid cavity. The measurement of the fluid conductivity also requires a change in the instrument to account for the different sensitivity of a two- and three-toroid cell. When used with a microprocessor, the sensitivity may easily be changed when the digital program is used for cell measurement. If a toroid output is doubled, the scaling of the microprocessor will be one-half as much.

The preferred configuration uses two outer drive toroid coils, and a single receiving toroid coil in the center. The three toroids are separated by grounded shields which reduce the unwanted direct signal transfer between the toroids. These shields confine the magnetic field to the bore area where the fluid to be measured is located. The shields also provide for greater isolation of the toroids when the liquid to be measured is absent.

The three-toroid electrodeless conductivity cell of this invention permits accurate conductivity measurement of low conductivity fluids. The two-toroid devices of the prior art suffer from noise and gain problems when taking low conductivity measurements. This invention reduces noise problems where low conductivity measurements are made by (1) shielding the receiving coil from noise generated in the solution being measured, and (2) the signal from the three-toroid configuration is twice as large as that from a two-toroid cell with the same cell factor.

Substantial shielding of the center receiving coil is provided by the drive coils which surround it. This drive coil shielding is in addition to the metallic shields which separate the toroids of this invention.

An important feature of this invention derives from the fact that the three-cell design with switch selectable coil configurations permits making measurements over a greater range than is possible with a conventional two-toroid cell. Two ranges are readily available. A measurement may be made with a single toroid connected as a drive coil and another toroid connected as a sense coil to measure a first range of values, then an additional toroid is connected in parallel with either the drive coil or the sense coil to double the sensitivity of the instrument. In order to make temperature compensated measurements from 0 to 120 degrees Centigrade with a two-toroid cell on a 1 microsiemens/cm range the instrument must ordinarily be capable of measuring up to 3.5 microsiemens/cm. By using the present three-toroid cell and switching out the second drive toroid, and thereby doubling the electrical cell factor, the instrument can measure up to 7.0 microsiemens/cm and thus compensate over a wider temperature range. A thermosensor may be included to sense temperature.

When a second drive toroid is added in parallel with the first toroid of a two-toroid cell, the current in the instrument will be doubled for a given probe, and the apparent electrical cell factor will be doubled. This apparent reduction of the cell factor results in an increase in the measurement range of the overall instrument, as the measuring circuit voltage gain requirement is reduced. For a given measuring circuit voltage gain, the probe sensitivity is thus doubled.

When a third toroid is added to an existing two-toroid cell, the physical cell factor can be reduced by about 67% because the length of the bore will be increased by one-half due to the thickness of the third toroid which is added to the cell length.

DESCRIPTION OF THE DRAWING FIGURES

The foregoing and other objects, features and advantages of the present invention will become more apparent in view of the foregoing and the accompanying detailed description of a preferred embodiment thereof as illustrated in the accompanying drawing figures, in which.

DETAILED DESCRIPTION OF THE PREFERRED EMBODIMENT

Figure 1:
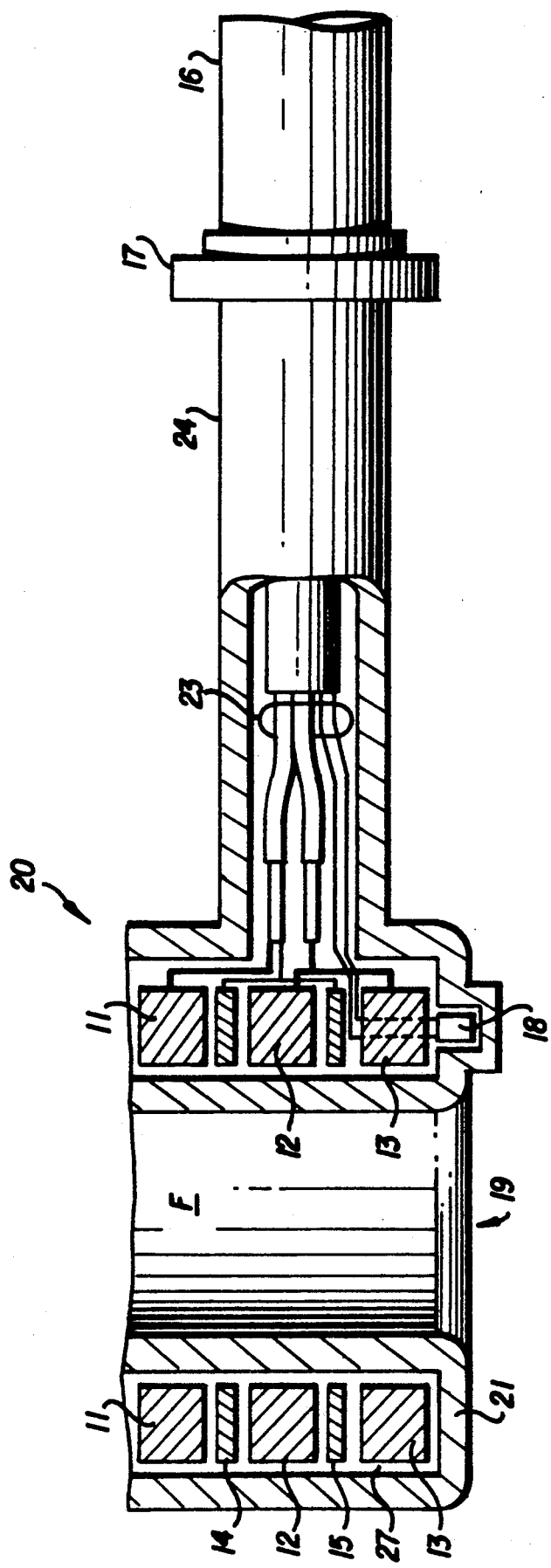
FIG. 1 shows a sectional view of apparatus in accordance with this invention showing the three toroids in cross section.

In FIG. 1 the three coaxial toroids 11, 12 and 13 are shown in cross section to illustrate the structure of a preferred embodiment of this invention. The central toroid 12 is selectively used as a receiving or sensing toroid subjected to the magnetic flux coupled to it from the drive toroids 11 and 13 by the fluid. The drive and sensing toroids may also be selectively reversed so that the center toroid 12 becomes drive and the end toroids 11 and/or 13 are used for sensing. This configuration is useful in measurement and instrument validation, and may be used where immunity from magnetic fields is not of paramount importance.

It has been found that the maximum sensitivity and minimum noise can be obtained when the sensing toroid 12 is isolated from the rest of the fluid by locating the sensing toroid between the two drive toroids.

FIG. 1 also shows magnetic shields 14 and 15 which are used to limit direct induction from the drive toroids 11 and 13 to the sensing toroid 12. These shields are flat, washer-like separators which are preferably grounded. These shields can also be described as thin centrally-apertured disc-shaped metallic separators which lie between the sensing and drive toroids.

The measuring cell 20 of FIG. 1 includes a magnetically transparent housing 21 in the shape of a closed dual annulus which encloses the toroids 11, 12 and 13 to form a fluid passageway bore 19; this housing 21 also prevents the fluid to be measured from entering into the toroidal windings and the interstitial cavities 27 between the toroids. The housing 21 includes an extension 24 which protects the connective wiring 23 to the measuring cell and which housing 21 is also useful for manipulating the cell 20 bore 19 end into a fluid F whose conductivity is to be measured. A peripheral flange 17 minimizes splashing and provides a convenient site for joining a further extension 16.

Note that it may be useful or necessary to include an additional sensor, such as a thermosensor 18 in a position effective for measuring the desired characteristic on or within the probe housing.

Although not shown, the three-toroid measuring cell according to this invention may be used with other physical constructions, such as where the center of the toroid is a pipe section which carries the fluid to be measured. Any other means of introducing the fluid into the bore 19 within the toroids may be used.

Figure 2:
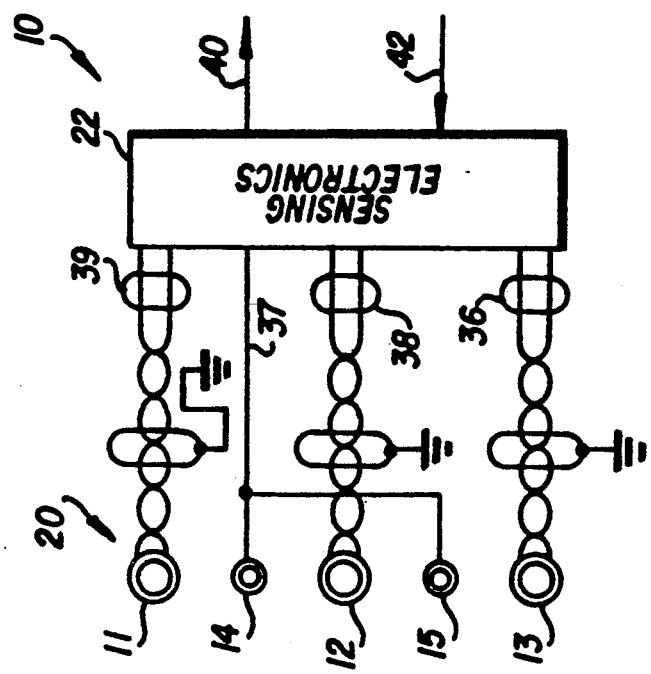
FIG. 2 shows schematically the measurement cell connected to a microprocessor-based sensing electronics package as for measurement and determination of cell cavity fluid integrity.

FIG. 2 is a schematic diagram of the invention 10, showing a package of sensing electronics 22 with connections to a measuring cell 20. The separators 14 and 15 are connected to ground via lead 37 to the sensing electronics 22. The drive toroid coils 11 and 13 shown are connected in parallel within the sensing electronics 22 by switching control circuits in SWITCHING CONTROL block 34, not visible in this view (see FIG. 3) and which are described hereinafter.

The SWITCHING CONTROL block 34, in combination with the three-cell design having switchable coils according to the present invention makes possible electrical conductivity measurements over a greater range than is possible with a simple two-toroid cell. Typically, two ranges are made available with the switching circuits in SWITCHING CONTROL block 34. A measurement is first made with one of the single toroids connected as a drive coil and another (preferably adjacent) toroid connected as a sense coil to measure a first range of fluid conductivity values, then an additional toroid is connected in parallel with either the drive coil or the sense coil to double the sensitivity of the instrument. For example, the switching circuits of SWITCHING CONTROL block 34 are capable of connecting outer toroid 11 to the DRIVE source 30 (see FIG. 3) via cable 39 as the only drive coil and connecting the center toroid 12 to the DETECTION block 32 via cable 38 as the only sense coil for obtaining one range of conductivity reading, in much the same configuration as with conventional two-toroid conductivity cells. Then an additional toroid 13 may be connected in parallel with the drive toroid 11 via cable 36 and the switching circuits to double the drive signal (increasing sensitivity by increased drive).

Alternatively, toroid 12 may be connected via cable 38 and the switching circuits of SWITCHING CONTROL block 34 as the drive coil and toroid 11 may be connected via cable 39 and the switching circuits as the sense coil for the first measurement, then an additional toroid 13 may be connected in parallel with the sense coil 11 via cable 36 and the switching circuits to double the pickup sensitivity (increasing sensitivity by increasing the pickup voltage). Sensitivity may also be decreased by a predeterminable degree to provide greater span by using the outer two toroids as a conventional two-toroid cell with a lower cell factor due to the increased length of the cell bore.

In order to make temperature compensated measurements from 0 to 120 degrees Centigrade with a two-toroid cell in the 1 microsiemens/cm range, the instrument must ordinarily be capable of measuring up to 3.5 microsiemens/cm. By using the present three-toroid cell in a two-toroid drive, one-toroid sense configuration and switching out the second drive toroid via the switching circuits under control of SWITCHING CONTROL block 34, thereby doubling the electrical cell factor, the instrument can measure up to 7.0 microsiemens/cm and thus compensate over a wider temperature range.

When a second drive toroid is added in parallel with the first toroid of a two-toroid cell, the cell current in the probe will be doubled for a given cell length, and the electrical cell factor is then cut in half, providing a doubled sensed voltage. Thus a greater output is available from the measuring circuit amplifier for a given gain factor. Reduction of the cell factor results in an increase in the measurement range of the instrument.

Also, adding a third toroid to an existing two-toroid cell reduces the physical cell factor by 67% because the length of the bore will be increased one-third due to the thickness of the third toroid which is added to the cell length.

If it is desired to perform a diagnostic sequence such as to determine if any leakage of fluid into the cell cavity 27 has occurred, additional connections from each toroid coil can be supplied at the sensing electronics 22. Sensing electronics 22 is to include drive and detect circuitry for determining fluid conductivity as is known to those of ordinary skill in the art. Similarly, SWITCHING CONTROL block 34 may include conventional switching circuitry conveniently located within the sensing electronics package to enable switching drive coils into and out of the circuit, and to exchange drive and detection circuitry on the sensing electronics 22 among the toroids. Enhanced and/or remote control switching may be performed by a microprocessor operating under a set of predetermined instructions, if desired. The microprocessor is to be capable of making measurements of the conductivity of the fluid and of the operating characteristics of the cell, such as fluid leakage into the cell cavity.

The three-toroid measurement cell is easily converted to a two-toroid device such as is known in the art. This conversion can be made by merely disconnecting either of the toroid coils 11 or 13 from the parallel circuit under control of the SWITCHING CONTROL block 34, described hereinafter. The disconnection may be configured to allow the remaining drive toroid coil and sensing toroid coil to function as a conventional two-toroid measuring cell. These connections and disconnections may be accomplished remotely, or manually at the sensing electronics 22 package via manual control of a conventional switching actuator 31.

This invention provides for the detection of a malfunction, such as fluid leakage into the toroid interstices in the cell cavity 27, by taking two or more differing toroid configuration readings of the conductivity of the fluid where the conductivity is known to be constant. The first measurement is made with two toroid drive coils as shown in FIGS. 1 and 2. The next measurement is taken with one of the toroid drive coils disconnected, which changes the electrical and mechanical configuration to a two-toroid configuration. When the configuration is changed from two drive toroids to only one drive toroid, the output of the remaining sense toroid coil will decrease from the previous measurement, assuming the fluid electrical conductivity remains the same. This feature enables the instrument to be used for multiple-range measurement, as the addition of the extra coil (or deletion thereof) from either the drive or sense coil circuit, or by switching from a two-toroid configuration to a three-toroid configuration enables variation of the cell factor, the drive power, and the sensing sensitivity. Compensation for the different cell factors and output characteristics may be performed electronically by sensing electronics 22 or remotely if operated under remote computer control.

Figure 3:
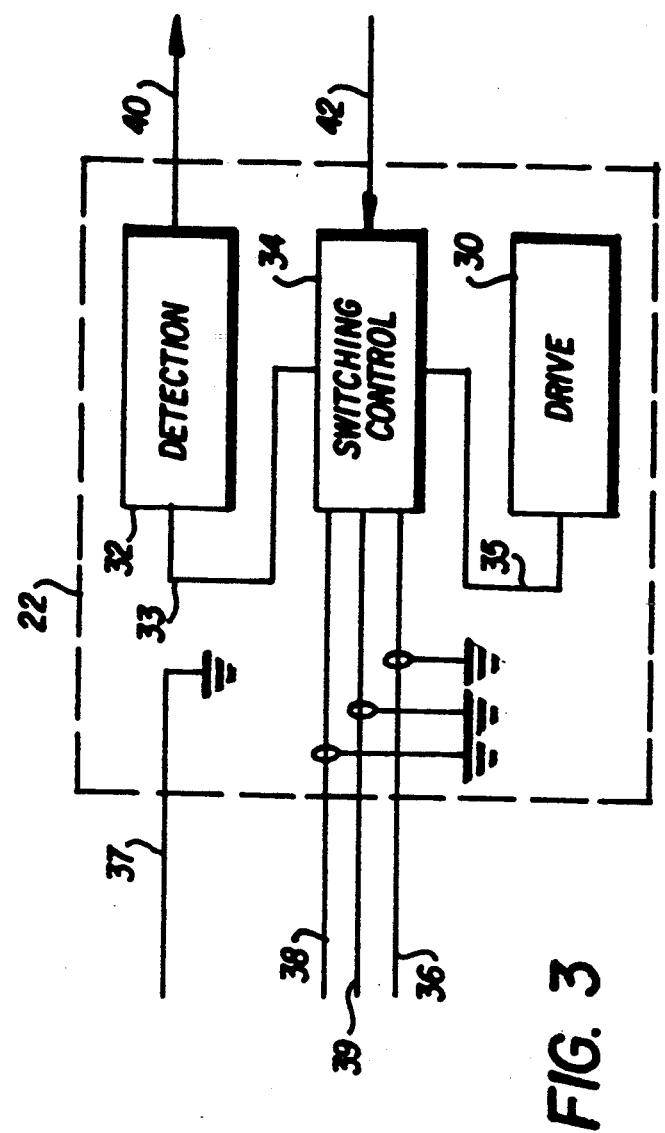
FIG. 3 illustrates the sensing electronics and switching apparatus enabling operation of the conductivity cell.

FIG. 3 shows a block diagram of the sensing electronics package 22. For the purposes of this disclosure, the three-toroid conductivity cell will be described in its conventional configuration, wherein the outer toroids 11, 13 are used as the drive coils and inner toroid 12 is used as the sense coil. Sensing electronics package 22 includes communication lines 40 and 42 to external indicating and/or measurement equipment, not forming a part of the present invention, and a plurality of communication lines 36, 38, and 39 interconnecting the sensing electronics package 22 with the probe 20. Lines 36, 38, and 39 may comprise conventional twisted-pair lines, shielded lines including shielded twisted-pairs, twin conductor coaxial cable, or multiple-shield cables, as are known to those of skill in the art. A separate ground lead 37 may be provided; the artisan of ordinary skill will recognize the great importance of good engineering practice in providing suitable earth/ground references for the probe 20 and the sensing electronics package 22. The drive signal is generated locally in DRIVE block 30, providing an electrical signal to the drive coil via line 35 to the switching circuits and via the signal lines 36 and 39, which may be shielded. An ac electrical signal is preferred. Signal line 38 (which also may be shielded) conveys the sensed signal from the sensing toroid to a conventional DETECTION block 32 via the switching circuits in SWITCHING CONTROL block 34 and line 33. The DETECTION block 32 provides a measurement output signal on line 40. Note that the DETECTION block 32 may include advanced signal processing, such as a processor under program control. Known switching circuits (FIG. 4) are included in SWITCHING CONTROL block 34 to connect and reconnect the toroid coils in different configurations, as required for test and validation operations previously described. Control line 42 controls actuator 31 to select from the many switching functions required to carry out this function. If under external or remote control, the switching circuits in SWITCHING CONTROL block 34 may be remotely controlled via control line 42.

Figure 4:
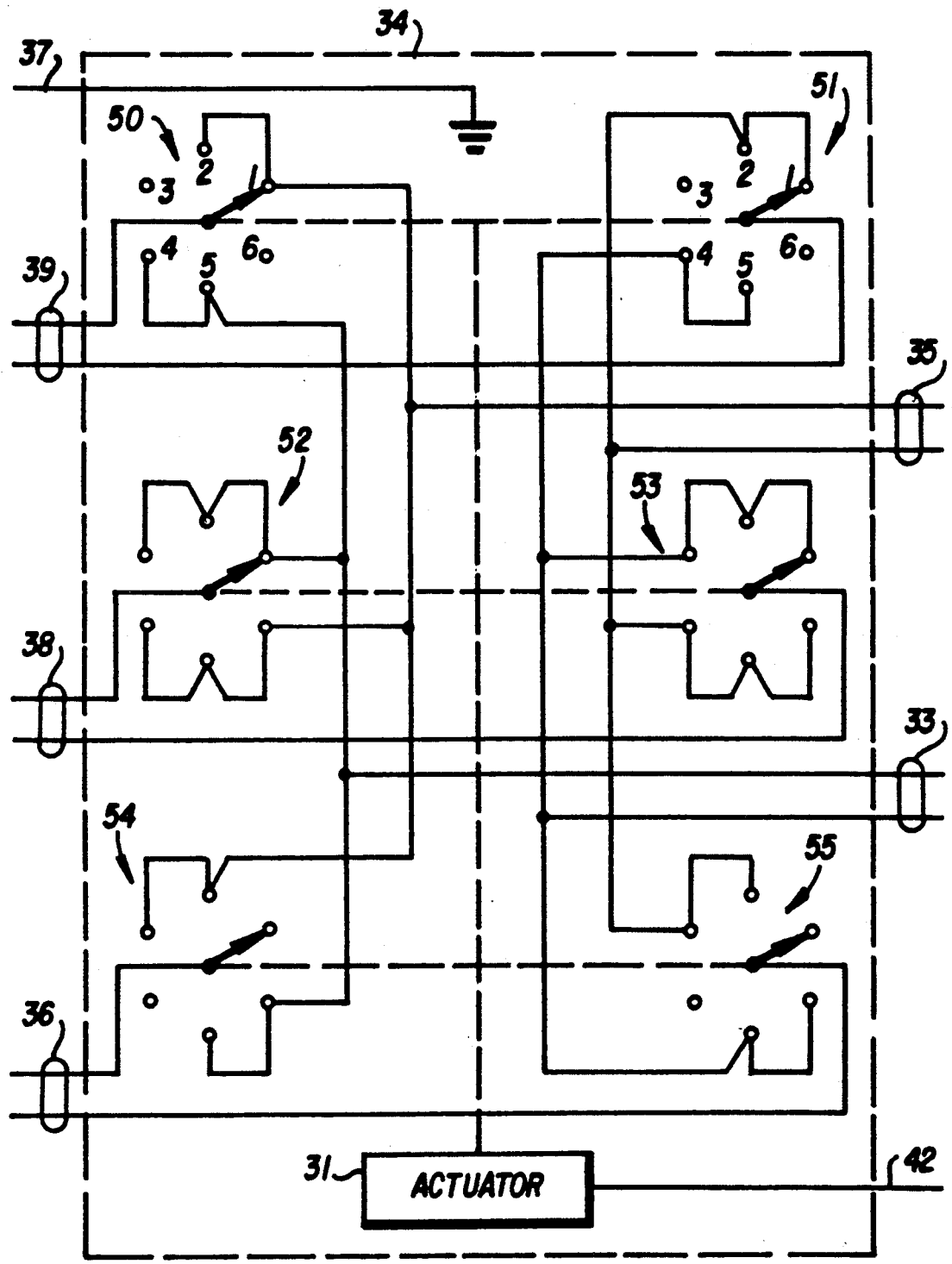
FIG. 4 illustrates a simple switching unit for selectively connecting the toroids in various configurations.

An example of the switching circuitry useful in this configuration is illustrated in FIG. 4. Here, the three toroid coils 11, 12, 13 are connected according to Table 1, indicating one group of possible switching circuit connection possibilities. Those of ordinary skill in the art will recognize that variations in the wiring of the switches 50-55 may be used to provide a different switch function order for the various toroid connection configurations.

TABLE 1

| TOROID REFERENCE NUMBER CONNECTED AS: | | | |
|---|---|---|---|
| 11 | 12 | 13 | SWITCH POSITION |
| Drive | Sense | N/C | 1 |
| Drive | Sense | Drive | 2 |
| N/C | Sense | Drive | 3 |
| Sense | Drive | N/C | 4 |
| Sense | Drive | Sense | 5 |
| N/C | Drive | Sense | 6 |

Here, a plurality of switches 50 through 55 in SWITCHING CONTROL block 34 provide the switching functions corresponding to TABLE 1. An actuator 31, which may be a manually operated switch shaft coupled to the respective switch shafts 50-55, or an electric or electronic switching circuit, selects the toroid connection configuration desired; the actuator 31 may be controlled remotely if desired and so equipped.

Although the invention has been shown and described with respect to a best mode embodiment thereof, it should be understood by those skilled in the art that the foregoing and various other changes, omissions and deletions in the form and detail thereof may be made therein without departing from the spirit and scope of this invention.

I claim:

1. An apparatus for measuring the conductivity of a fluid, comprising:
    a housing;
    first, second, and third toroids axially spaced along a common central axis in said housing and having an input sinusoidal voltage and current, including means for generating a magnetic field in said fluid, and means for magnetic flux sensing all disposed in said housing within said fluid, said means for magnetic flux sensing having an electrical output,
    wherein said first and second toroids are magnetically aligned so that the magnetic field interacts with said third toroid to induce a voltage and current in said third toroid, further including a magnetic shield at least partially surrounding the third toroid, wherein said magnetic shield comprises first and second centrally apertured discs arranged to separate said first, second, and third toroids, wherein said magnetic flux including means comprises two toroids electrically connected together in parallel, wherein said first, second, and third toroids have substantially the same inside and outside diameters and are disposed coaxially within said housing to form a single bore for fluid passage therethorugh, and further including a thermosensor means disposed within said housing for measurement compensation based on fluid temperature.

2. The apparatus of claim 1 wherein said third toroid lies between said first and second toroids in the center thereof.

3. The apparatus of claim 2 further including means for sensing the voltage and current induced by said first and second toroids in said third toroid.

4. The apparatus of claim 1 wherein said magnetic shield is grounded.

5. The apparatus of claim 1 wherein the toroids form a cylinder-shaped bore and said magnetic shield reduces unwanted signal transfer between the toroids.

6. The apparatus of claim 1, wherein said electrical current is alternating current.

7. Apparatus for measuring the electrical conductivity of a fluid, comprising:
    a sandwich of first, second, and third toroids, each having a centrally located aperture surrounding an axis, the toroids being stacked together coaxially to form a bore permitting fluid passage therein;
    a magnetically transparent housing enclosing said toroids;
    a source of electrical current;
    mean for inducing a magnetic flux in the fluid passage by application of said electrical current to at least one of said toroids;
    means for sensing the magnetic flux coupled to at least one of said toroids; and
    switch means for selectively connecting each of said first, second, and third toroids as the magnetic flux including means in the fluid passage, and alternatively as the magnetic flux sensing means.

8. The apparatus of claim 7, wherein said magnetic flux inducing means comprises two toroids electrically connected together in parallel.

9. The apparatus of claim 8, wherein said magnetic flux inducing means comprises two toroids surrounding said magnetic flux sensing means.

10. The apparatus of claim 7, wherein said magnetic flux sensing means comprises two toroids electrically connected together in parallel.

11. The apparatus of claim 10, wherein said magnetic flux sensing means comprises two toroids surrounding said magnetic flux inducing means.

12. The apparatus of claim 7, further including a thermosensor disposed within said housing.

13. The apparatus of claim 7, wherein said electrical current is alternating current.

14. In combination, apparatus for measuring the electrical conductivity of a fluid, comprising:
    a sandwich of first, second, and third toroids, each having a centrally located aperture surrounding an axis, the toroids being stacked together coaxially to form a bore permitting fluid passage therein;
    a magnetically transparent housing enclosing said toroids;
    a source of electrical current;
    means for inducing a magnetic flux in the fluid passage by application of said electrical current to at least one of said toroids;
    means for sensing the magnetic flux coupled to at least one of said toroids; and
    means for measurement validation comprising means for selectively connecting and disconnecting each of said first, second, and third toroids as the magnetic flux inducing means in the fluid passage, and alternatively as to magnetic flux sensing means.

15. The apparatus of claim 14, wherein said magnetic flux inducing means comprises two toroids electrically connected together in parallel.

16. The apparatus of claim 15, wherein said magnetic flux inducing means comprises two toroids surrounding said magnetic flux sensing means.

17. The apparatus of claim 14 wherein said magnetic flux sensing means comprises two toroids electrically connected together in parallel.

18. The apparatus of claim 17, wherein said magnetic flux sensing means comprises two toroids surrounding said magnetic flux inducing means.

19. The apparatus of claim 18, further including a thermosensor disposed within said housing.

20. The apparatus of claim 14, wherein said electrical current is alternating current.

21. In combination, apparatus for measuring the electrical conductivity of a fluid, comprising:
- a sandwich of first, second, and third toroids, each having a centrally located aperture surrounding an axis, the toroids being stacked together coaxially to form a bore permitting fluid passage therein;
- a magnetically transparent housing enclosing said toroids;
- a source of electrical current;
- means for inducing a magnetic flux in the fluid passage by application of said electrical current to at least one of said toroids;
- means for sensing the magnetic flux coupled to at least one of said toroids; and
- means for measurement range selection comprising means for selectively connecting and disconnecting each of said first, second, and third toroids as the magnetic flux inducing means in the fluid passage, and alternatively as the magnetic flux sensing means.

22. The apparatus of claim 21, wherein said magnetic flux inducing means comprises two toroids electrically connected together in parallel.

23. The apparatus of claim 22, wherein said magnetic flux inducing means comprises two toroids surrounding said magnetic flux sensing means.

24. The apparatus of claim 21, wherein said magnetic flux sensing means comprises two toroids electrically connected in parallel.

25. The apparatus of claim 24, wherein said magnetic flux sensing means comprises two toroids surrounding said magnetic flux inducing means.

26. The apparatus of claim 21, further including a thermosensor disposed within said housing.

27. The apparatus of claim 21, wherein said electrical current is alternating current.

28. A method of measurement validation with a fluid conductivity meter including a sandwich of at lest three toroids stacked together coaxially to form a bore permitting fluid passage therein, and a source of electrical current, comprising:
- inducing a magnetic flux in the fluid passage by application of said electrical current to a first one of said toroids;
- sensing the magnetic flux coupled to a second one of said toroids;
- selectively connecting the third toroids as the magnetic flux inducing means in the fluid passage; an
- comparing the sensed magnetic flux before and after connecting the third toroid.

29. A method of measurement validation with a fluid conductivity meter including a sandwich of at least three toroids stacked together coaxially to form a bore permitting fluid passage therein, and a source of electrical current, comprising:
- inducing a magnetic flux in the fluid passage by application of said electrical current to a first one of said toroids;
- sensing the magnetic flux coupled to a second one of said toroids;
- selectively connecting the third toroid as the magnetic flux sensing means; and
- comparing the sensed magnetic flux before and after connecting the third toroid.

30. A method of measurement range switching in a fluid conductivity meter including a sandwich of at least three toroids stacked together coaxially to form a bore permitting fluid passage therein, and a source of electrical current, comprising:
- inducing a magnetic flux in the fluid passage by application of said electrical current to a first one of said toroids;
- sensing the magnetic flux coupled to a second one of said toroids;
- selectively connecting the third toroid as the magnetic flux inducing means in the fluid passage; and
- measuring the sensed magnetic flux.

31. The method of measurement range switching in a fluid conductivity meter including a sandwich of at least three toroids stacked together coaxially to form a bore permitting fluid passage therein, and a source of electrical current, comprising:
- inducing a magnetic flux in the fluid passage by application of said electrical current to a first one of said toroids;
- sensing the magnetic flux coupled to a second one of said toroids;
- selectively connecting the third toroid as the magnetic flux sensing means; and
- measuring the sensed magnetic flux.

32. An apparatus for measuring the conductivity of a fluid, comprising:
- a housing;
- first, second, and third toroids axially spaced along a common central axis in said housing and having an input sinusoidal voltage and current, including means for generating a magnetic field in said fluid, and means for magnetic flux sensing disposed in said housing within said fluid, said means for sensing having a central axis and an electrical output,
- wherein said third toroid is magnetically aligned so that the magnetic field interacts with said first and second toroids to induce a voltage and current in said first and second toroids, further including a magnetic shield at least partially surrounding said first and second toroids, wherein said magnetic flux sensing means comprises two toroids electrically connected together in parallel, wherein said first, second, and third toroids have substantially the same inside and outside diameters and are substantially coaxial within said housing to form a single bore for fluid passage therethrough, wherein said magnetic shield comprises first and second centrally apertured discs, arranged to separate said first, second, and third toroids, and further including a thermosensor means disposed within said housing for measurement compensation based on fluid temperature.

33. The apparatus of claim 32 wherein said third toroid lies between said first and second toroids in the center thereof.

34. The apparatus of claim 33 further including means for sensing the voltage and current induced by said third toroid in said first and second toroids.

35. The apparatus of claim 32 wherein said magnetic shield is grounded.

36. The apparatus of claim 32 wherein the first, second, and third toroids form a cylinder-shaped bore and said magnetic shield reduces unwanted signal transfer between the toroids.

37. The apparatus of claim 32, wherein said electrical current is alternating current.

* * * * *